United States Patent [19]
Fischer et al.

[11] Patent Number: 6,071,964
[45] Date of Patent: Jun. 6, 2000

[54] DICLOFENAC/GAMMA-CYCLODEXTRIN INCLUSION COMPOUNDS

[75] Inventors: Wilfried Fischer; Anna Sendl-Lang, both of Holzkirchen, Germany

[73] Assignee: Hexal AG, Holzkirchen, Germany

[21] Appl. No.: 09/155,298

[22] PCT Filed: Mar. 27, 1997

[86] PCT No.: PCT/EP97/01595

§ 371 Date: May 11, 1999

§ 102(e) Date: May 11, 1999

[87] PCT Pub. No.: WO97/35568

PCT Pub. Date: Oct. 2, 1997

[30] Foreign Application Priority Data

Mar. 27, 1996 [HU] Hungary ................... 9600758

[51] Int. Cl.[7] ............................ A61K 31/195
[52] U.S. Cl. ............................ 514/567; 514/922
[58] Field of Search ....................... 514/567, 922

[56] References Cited

FOREIGN PATENT DOCUMENTS

| | | |
|---|---|---|
| 0 446 753 A1 | 9/1991 | European Pat. Off. . |
| 0 510 561 B1 | 10/1992 | European Pat. Off. . |
| 0 519 428 A2 | 12/1992 | European Pat. Off. . |
| 0 446 753 B1 | 11/1994 | European Pat. Off. . |
| 0 647 451 A1 | 4/1995 | European Pat. Off. . |
| 0 371 431 B1 | 6/1995 | European Pat. Off. . |
| 0 658 347 A2 | 6/1995 | European Pat. Off. . |
| 42 07 922 A1 | 9/1993 | Germany . |
| WO92/00725 | 1/1992 | WIPO . |
| WO94/28936 | 12/1994 | WIPO . |
| WO95/01781 | 1/1995 | WIPO . |

OTHER PUBLICATIONS

Backensfeld et al., "Interacton of NSA with cyclodextrins and hydroxypropyl cyclodextrin derivatives", International Journal of Pharmaccutics, 74 (1991) pp. 85–93.

Devi et al., "Albumin Microspheres and Betacyclodextrin Inclusion Complex Containing Diclofonac Sodium", Indian Journal of Pharmaceutical Sciences, Nov.–Dec. 1992, pp. 259–261.

Orienti et al., "Availability of NSAIDH β–Cyclodextrin Inclusion Complexes", Arch. Pharm. (Weinheim) 322, 207–211 (1989).

Abstract Printed from the Cyclodextrin News Library Database, CA: 115:239451, "Inclusion complexes between non steroidal antiinflammatory drugs and beta–cyclodextrin" (1991).

Abstract Printed from the Cyclodextrin News Library Database, "Preparation and evaluation of Flurbiprofen and Diclofenac sodium transdermal films" (1993).

Backensfeld, Pharmazeutisches Institut der Christian Albrechts Universitat Kiel., Arch. Pharm. 323, 690 (1990).

*Primary Examiner*—Kimberly Jordan
*Attorney, Agent, or Firm*—Brooks & Kushman P.C.

[57] ABSTRACT

The object of the present invention is an oral drug preparation containing the γ-cyclodextrin complex of diclofenac or pharmaceutically acceptable salts thereof, especially the sodium salt prepared by known methods, and by which the gastro-intestinal irritancy of diclofenac, at the same or improved bioavailability, can be considerably decreased.

14 Claims, No Drawings

DICLOFENAC/GAMMA-CYCLODEXTRIN INCLUSION COMPOUNDS

Diclofenac.sodium (chemical name 2-[(2.6-dichlorophenyl)amino]benzeneacetic acid sodium salt) is an effective and widely used non-steroid anti-inflammatory agent marketed as Voltaren® (Ciba Geigy) in several countries.

Diclofenac is applied in different formulations such as tablet, film tablet, dragée, capsule, retard preparations, injection, suppository, ophthalmic solution, gel.

The most frequently applied tablet formulation—similarly to other poorly soluble, slowly absorbed non-steroid anti-inflammatory drugs—causes local irritation in the stomach especially in case of chronic treatment.

Cyclodextrins are cyclic oligosaccharides consisting of 6, 7 or 8 α-D-glucopiranose units in which the glucose units are linked by α,1→4 linkage. The eight-member ring is called γ-cyclodextrin. Cyclodextrins form inclusion complexes with the hydrophobic guest molecules of appropriate size. Cyclodextrins, cyclodextrin derivatives, inclusion complexation process and characterization of complexes are widely discussed by Szejtli (Cyclodextrins and Their Inclusion Complexes, Akadémiai kiadó, Budapest, 1982. Cyclodextrin Technology, Kluwer Academic Publishers, Dordrecht, 1988) and Frömming and Szejtli (Cyclodextrins in Pharmacy, Kluwer Academic Publishers, Dordrecht/Boston, 1994).

Diclofenac—similarly to other non-steroidal anti-inflammatory drugs—shows toxic side effects; it irritates the gastrointestinal mucosa, bleedings, ulcers and perforations may develop. The development of ulcers is a complex process, involving many factors: damage of the mucosal barrier, inhibition of the mucosal prostanoid synthesis, direct effect on the cellular enzymes, increased acid secretion, slowing down of repair processes etc. Dose of the given drug, route of administration, metabolism etc. may also play a role. The effect of a certain factor may change from drug to drug.

Preparation and pharmaceutical applications of diclofenac/cyclodextrin complexes are described in several patents.

Eye drops containing diclofenac sodium and β-cyclodextrin for enhancement of the solubility of the poorly soluble diclofenac are described in a Japan Kokai 58174310 (Wakamoto Pharm. Co., Ltd. 1982).

The Japan Kokai 590848821 (Teikoku Chemical Industry Co., Ltd. 1982) describes sustained-release analgesics containing diclofenac and β-cyclodextrin.

The Japan Kokai 62289515 (Ishida. K:, 1986) describes lint cloth coated with medicine containing diclofenac and cyclodextrin.

A medical preparation used for treatment of ischaemic brain diseases is discussed in the Japan Kokai 62198616 (Shingijutsu Kaihatsu K.K., 1986), the preparation contains a prostaglandin synthesis inhibitor e.g. diclofenac and cyclodextrin.

Suppositories containing steroid and non-steroid anti-inflammatory drugs—e.g. diclofenac and cyclodextrin are described in the Japan Kokai 87,138.437 (Nakanishi, M. 1987). Cyclodextrin is used as an absorption promoter.

EP 371431 (Vectorpharma International S.p.A., 1988) describes the preparation of supported drugs with increased dissolution rate. The drug and the support material are co-ground in a mill with its grinding chamber saturated with solvent vapour. The solvent solubilizes the drug or promotes its adsorption onto the support material.

This technology decreases the extent of drug crystallinity. The drug can be e.g. diclofenac, the support material may be cyclodextrin polymer or water-soluble cyclodextrin.

The EP 446753 (Vectorpharma International S.p.A., 1990) deals with therapeutic compositions with controlled release of medicaments. The drug is supported on crosslinked polymer matrix which is insoluble but swellable in water.

The drug can be e.g. diclofenac, the polymer matrix is, for example, water-insoluble cyclodextrin polymer.

The WO 92/00725 patent application (Farcon AG, 1990) describes oral topical liquid pharmaceutical compositions of non-steroidal anti-inflammatory drugs e.g. diclofenac. Combining the drugs with cyclodextrins or cyclodextrin derivatives (physical mixture, complex, coprecipitate) is suggested. Cyclodextrins can be α-, β-, γ-cyclodextrin or hydroxypropyl-β-cyclodextrin.

The objects of the EP 510561 patent (Poli Industria Chimica S.p.A., 1991) are oral, dermal and intravaginal liquid pharmaceutical compositions in the form of foam. The drug can be—among many others—diclofenac, or its cyclodextrin complex.

The DE 4207922 German patent (Pharmatech GmbH) describes the water soluble inclusion complex of diclofenac sodium with methylated β-cyclodextrins or with hydroxypropyl-β-cyclodextrin.

The Japan Kokai 06016547 (Wakamoto Pharm. Co. Ltd. 1992) describes eye-drops containing diclofenac sodium and enzymatically or chemically modified β-cyclodextrin derivatives.

The patent of Takeda Chemical Industies, Ltd (EP 519.428, 1992) describes a pharmaceutical composition containing a cyclodextrin and a poorly water soluble drug e.g. diclofenac.

The composition contains water-soluble organic solvent, especially for injections.

The WO 94/28936 patent application (Ciba-Geigy. 1993) relates to a novel advantageous process for the preparation of an oral solid dosage containing diclofenac (or salts thereof). The dosage form is obtainable by direct compression of the γ-cyclodextrin inclusion complex of diclofenac and the salts thereof. The examples describe complexes of 1:1 molar ratio.

The EP 647451 patent (South African Druggist Ltd., 1993) describes the inclusion complex of diclofenac (or salts thereof) and non-substituted β-cyclodextrin.

The WO 95/01781 (APR Applied Pharma Research SA, 1993) describes multilayered controlled-release oral solid pharmaceutical forms, The drug can be diclofenac sodium. In the first layer which is intended to release a drug portion in short times, there is a polymer, e.g. β-cyclodextrin.

The EP 658347 patent describes the method of preparing an injectable pharmaceutical or veterinary composition (South African Druggist Ltd. 1993) containing diclofenac (or salts thereof) and 2-hydroxypropyl-β-cyclodextrin. The injectable composition is applied for the inhibition of prostaglandin synthesis. The composition may contain an inclusion complex or the mixture of drug and cyclodextrin. Pharmacokinetic studies performed on human volunteers have shown that the preparation formulated by cyclodextrin and administered intramuscularly is bioequivalent with the marketed diclofenac sodium injection, but in case of the cyclodextrin-containing injection, higher plasma concentration can be attained within a shorter time.

The WO 95/32737 patent application (South African Druggist Ltd., 1994) describes the preparation method of a solid pharmaceutical composition consisting of β-cyclodextrin or a derivative thereof (hydroxypropyl or methyl βCD) and a poorly water soluble non-steroid anti-inflammatory drug e.g. diclofenac sodium. The composition, which is an inclusion complex of the drug is prepared by the kneading method and dried at 40° C. The solid product when dissolved in water. gives a clear or slightly opalescent solution which is suitable for oral use.

All these inventions and patents describe preparation methods of inclusion complexes of diclofenac with a cyclodextrin which methods have been well-known for a long time and widely applied. The aim verified empirically in each case is to achieve a faster dissolution and higher solubility of the drug which, according to the general experiences with the inclusion complexes of drugs is expressed in faster biological absorption and in improved bioavailability as well.

The inventions, patents and other publications related to diclofenac discussed above comprise several further results of physico-chemical studies such as X-ray diffraction studies of the crystal structure of diclofenac/cyclodextrin complexes, the study of interactions between diclofenac and cyclodextrin molecules in solution by nuclear magnetic resonance, Fourier-transformed infrared spectroscopic, differential-scanning calorimetric studies etc.

The overwhelming majority of the above mentioned inventions and patents applies β-cyclodextrin for complexation of diclofenac. At the time when these patents were worked out it had not been known yet that—according to the JECFA recommendations—the daily oral dose of β-cyclodextrin should not be beyond 6 mg/kg body weight. Namely, a small part of β-cyclodextrin is absorbed from the gastro-intestinal tract and may cause irreversible damage of the kidneys.

Therefore, oral diclofenac formulations containing β-cyclodextrin are not feasible since in case of all diclofenac/β-cyclodextrin complexes recommended for oral use this 6 mg/kg limit would be far exceeded.

Several reports deal with the preparation and characterization of diclofenac/cyclodextrin inclusion complexes. (E.g. Backensfeld. T. Mueller, B. W.: Arch. Pharm. 323 690, 1990; Backensfeld, T. Mueller, B. W., Kolter, K.: Int. J. Pharm. 74 (2–3). 85, 1991; Devi, S. G. Prakasam, K., Udapa, H.: Indian J. Pharm. Sci. 54 (6), 259, 1992; Orienti, I. Cavallari, C. Zecchi, V.: Arch. Pharm. 322, 207, 1989; Orienti, I., Fini, A. Bertasi, V., Zecchi, V.: Eur. J. Pharm. Biopharm,. 37 (2), 110, 1991: Singh, U. V., Pandey, S. Udupa, N.: Indian J. Pharm. 55 (4), 145, 1993;

The object of our invention is to decrease the side effect: namely the gastro-intestinal irritant, stomach and intestinal ulcer inducing effect of diclofenac by applying diclofenac in a formulation providing a fast dissolution and an enhanced bioavailability of the drug.

The main object of our invention is an oral pharmaceutical composition containing diclofenac in form of a diclofenac/γ-cyclodextrin complex prepared by known methods by which the gastro-intestinal irritant effect of diclofenac can be significantly decreased.

The problem underlaying the invention is solved by a chemical composition comprising at least 50% by weight of or consisting of an inclusion compound formed from diclofenac and γ-cyclodextrin at a molar ratio of about 1:2.

A specific embodiment of the invention concerns a chemical composition consisting of at least 50% by weight of the above mentioned inclusion compound, the remainder being diclofenac and/or an inclusion compound formed from diclofenac and a cyclodextrin other than an inclusion compound formed from diclofenac and γ-cyclodextrin at a molar ratio of about 1:2.

Further, a specific embodiment of the invention concerns a chemical composition, wherein the remainder is an inclusion compound formed from diclofenac and γ-cyclodextrin at a molar ratio of about 1:1.

Further, a specific embodiment concerns a chemical composition, wherein the composition comprises at least 80, preferably at least 90 and especially at least 95% by weight of the inclusion compound formed from diclofenac and γ-cyclodextrin at a molar ratio of about 1:2.

Further, a specific embodiment concerns a chemical composition, characterized in that diclofenac is present as a pharmaceutically acceptable salt thereof, especially as its sodium salt.

The problem underlaying the invention is further solved by a pharmaceutical preparation consisting of a chemical composition according to the invention or comprising same, optionally besides usual pharmaceutical adjuvants.

Further, a specific embodiment of the invention concerns a pharmaceutical preparation, wherein the preparation is a dry preparation at solid state.

Further, a specific embodiment of the invention concerns a pharmaceutical preparation, wherein the preparation is for oral purposes.

Finally, a specific embodiment of the invention concerns a pharmaceutical preparation, wherein the preparation is a granulate, a tablet or an effervescent tablet.

The diclofenac/γ-cyclodextrin complexes used for the irritation studies and for verification of absorption enhancement were prepared by two different, otherwise well-known methods.

"A" composition

Diclofenac sodium/γ-cyclodextrin complex of 1:2 molar ratio 0.708 g diclofenac sodium and 6.98 g γ-cyclodextrin were added to 34 ml distilled water and mixed with Ultra-Turrax T25 equipment for 4×2 minutes. The suspension was freeze dried.

Weight of the solid product: 7.6 g

Diclofenac sodium content: 9.5±0.5%

"B" composition

Diclofenac sodium/γ-cyclodextrin complex of 1:2 molar ratio 8.05 g diclofenac sodium and 87.0 g γ-cyclodextrin powders were mixed, then under continuous stirring they were added to 60 ml 60° C distilled water and stirred for 10 minutes. The creamy suspension was poured onto trays and dried at 50° C. During drying the substance was mixed several times in order to get a granulated product. At 4–5% water content the substance was meshed through a 2 mm sieve and dried further.

Weight of the solid product: 94 g

Water content: 6.15%

Diclofenac sodium content: 7.9%

The advantages of our invention are demonstrated by the following in vitro and in vivo results:

EXAMPLE 1

The gastric irritancy of diclofenac sodium/γCD complex ("B" composition, molar ratio 1:2) and that of diclofenac sodium were compared on Wistar male rats. The average body weight of the animals was 230 g. Fasted rats were treated with a single mg/kg body weight oral dose related to diclofenac. To one group of rats (20 rats) diclofenac sodium, to another group (20 rats) diclofenac sodium/γ-cyclodextrin complex and to a third group (10 rats) distilled water was given per os. Rats were dissected 4 hours after the treatment and the number and size of ulcers in the stomach were determined.

The ulcers were divided into four groups according to their size:

a./ the largest diameter is <1 mm,
b./ the largest diameter is between 1–2 mm
c./ the largest diameter is between 2–4 mm
d./ the largest diameter is >4 mm.

The number of ulcers was counted and the ulcer index was calculated as follows:

total number of ulcers <1 mm was multiplied by 0.5
total number of ulcers between 1 to 2 mm was multiplied by 1
total number of ulcers between 2 to 4 mm was multiplied by 2
total number of ulcers >4mm was multiplied by 3

The ulcer index was determined for each animal and total and mean values were given for the different groups. (Table I. and II.).

TABLE I

Gastroirritancy of diclofenac sodium
dose: 10 mg/kg

| No. of rats | Diclofenac sodium Number of ulcers | | | | Ulcer index |
|---|---|---|---|---|---|
| | <1 mm | 1–2 mm | 2–4 mm | >4 mm | |
| 1 | 1 | | | | 0.5 |
| 2 | | | | | 0 |
| 3 | 1 | | | | 0.5 |
| 4 | 8 | | | | 4 |
| 5 | 6 | 6 | | 1 | 12 |
| 6 | 1 | | | | 0.5 |
| 7 | 1 | | | | 0.5 |
| 8 | | | | | 0 |
| 9 | 7 | 3 | 2 | | 10.5 |
| 10 | | | | | 0 |
| 11 | 14 | 8 | 7 | 7 | 50 |
| 12 | | | | | 0 |
| 13 | 5 | | 2 | | 6.5 |
| 14 | | | | | 0 |
| 15 | | | | | 0 |
| 16 | 4 | 3 | 2 | | 9 |
| 17 | | | | | 0 |
| 18 | | | | | 0 |
| 19 | 4 | 2 | | | 4 |
| 20 | | | | | 0 |
| Total | 52 | 22 | 13 | 8 | 98 |
| Mean | | | | | 4.9 |

No ulcers were found in nine out of 20 rats treated with diclofenac sodium. Ulcers larger than 1 mm were observed in 5 rats, severe ulceration was found in one rat (No. 11, ulcer index: 50). The mean ulcer index was 4.9 in this group.

TABLE II

Gastroirritancy of Diclofenac sodium/γ-cyclodextrin complex
dose related to diclofenac sodium: 10 mg/kg
Diclofenac sodium/γ-cyclodextrin complex

| No. of rats | Number of ulcers | | | | Ulcer index |
|---|---|---|---|---|---|
| | <1 mm | 1–2 mm | 2–4 mm | >4 mm | |
| 1 | | | | | 0 |
| 2 | 1 | | | | 0.5 |
| 3 | 1 | | | | 0.5 |
| 4 | 5 | | | | 2.5 |
| 5 | | | | | 0 |
| 6 | 1 | | | | 0.5 |
| 7 | 7 | 4 | 3 | | 13.5 |
| 8 | | | | | 0 |
| 9 | | | | | 0 |
| 10 | | | | | 0 |
| 11 | 6 | | | | 3 |
| 12 | | | | | 0 |
| 13 | 11 | | 1 | | 7.5 |
| 14 | | | | | 0 |
| 15 | 1 | | | | 0.5 |
| 16 | 8 | 1 | | | 5 |
| 17 | | | | | 0 |
| 18 | | | | | 0 |
| 19 | | | | | 0 |
| 20 | | | | | 0 |
| Total | 41 | 5 | 4 | | 33.5 |
| Mean | | | | | 1.7 |

No ulcers were found in 11 rats, ulcers larger than 1 mm were observed in the stomach of 4 animals. The highest ulcer index was 13.5, the mean value was 1.7. No ulcers were found in any of the control animals.

The number of ulcers was significantly lower in the diclofenac sodium/γ-cyclodextrin complex-treated group than in the free diclofenac sodium-treated group.

Therefore, γ-cyclodextrin decreased the gastroirritant effect of diclofenac sodium considerably when applied as a single 10 mg/kg (related to diclofenac sodium) dose.

EXAMPLE 2

The gastro-intestinal irritancy of diclofenac sodium/γ-cyclodextrin complex ("A" composition) and that of free diclofenac sodium was compared in a subacute experiment on rats. Male Wistar rats weighing 220 g average were used. Animals were kept on a standard LATI rat and mouse chow before and during the experiment. Animals were treated orally with 15 mg/kg dose diclofenac sodium (10 rats) or the complex containing an equivalent amount of diclofenac sodium (10 rats) for 4 days as follows:

| 1st day | 15 mg/kg | at 8 a.m. |
|---|---|---|
| 2nd day | 15 mg/kg | at 8 a.m. |
| 3rd day | 15 mg/kg | at 8 a.m. and at 8 p.m. |
| 4th day | 15 mg/kg | at 8 a.m. |

Control rats were given 0.5% methylcellulose solution (5 animals). Four hours after the last treatment animals were dissected.

Ulcers, perforations and peritonitis developed as a result of this treatment and were evaluated according to the following scale:

0: normal condition 0.5: signs of inflammation in the small intestine, greyish-reddish discoloration of the intestinal wall, no perforation 1: at least 1 perforation, small adhesions 2: 2 or more perforations, larger adhesion parts in the intestine 3: perforations, large adhesions in the intestine including a few other organs 4: severe peritonitis, including practically all organs in the abdomen Results are shown in Table III.

Both in complex- and diclofenac sodium-treated groups perforations were observed in the jejuno-ileal part of the small intestine. However, the irritancy index was significantly lower in case of complex-treated rats (1.5) than in the diclofenac sodium-treated group (2.3). Therefore, it can be concluded that the diclofenac sodium/γ-cyclodextrin complex proved to be less toxic than diclofenac sodium in the subacute experiment.

TABLE III

Intestinal irritancy of diclofenac sodium and
diclofenac sodium/γ-cyclodextrin complex of 1:2 molar ratio
subacute experiment, dose related to diclofenac sodium: 15 mg/kg

| No. of rat | Irritancy index Diclofenac sodium | No. of rat | Irritancy index complex |
|---|---|---|---|
| 1 | 2 | 12 | 0.5 |
| 2 | 2 | 13 | 0.5 |
| 3 | 1 | 14 | 2 |
| 4 | 4 | 15 | 1.5 |
| 5 | 1 | 16 | 0.5 |
| 6 | 1.5 | 17 | 3 |
| 7 | 4 | 18 | 0.5 |
| 8 | 3 | 19 | 2.5 |
| 9 | 1 | 20 | 2 |
| 10 | 2.5 | 21 | 2 |
| 11 | 3.5 | 22 | 2 |
| | Mean: 2.3 | | Mean: 1.5 |

EXAMPLE 3

230 mg of diclofenac sodium/γ-cyclodextrin complex ("A" composition) were added to 20 ml simulated gastric juice (pH 1.2 HCl) and stirred for 30 minutes at 25° C. Samples of 4.4 ml each were taken at 0, 5, 10 and 30 minutes, filtered across a 0.45 μm membrane filter and dissolved diclofenac concentration was determined by UV-spectrophotometry.

Results are shown in Table IV.

TABLE IV

Dissolution of diclofenac sodium/γ-cyclodextrin
complex in pH 1.2 HCl

| Time (min) | Dissolved diclofenac sodium concentration (μg/ml) complex of 1:2 molar ratio according to the 1st example |
|---|---|
| 0 | 0 |
| 5 | 52.6 |
| 10 | 28.6 |
| 30 | 16.6 |

Complexation increased the dissolution of diclofenac in pH 1.2 HCl. (Under similar conditions, dissolution of non-complexed diclofenac sodium is less than 2 μg/ml in 30 minutes.) The complex of 1:2 molar ratio offered a concentration of dissolved diclofenac more than one order of magnitude higher than that of free diclofenac sodium in the first 10 minutes.

EXAMPLE 4

Fasted New Zealand white male rabbits weighing 2,4 kg average were treated orally with diclofenac sodium/γ-cyclodextrin complex ("B" composition) or diclofenac sodium. Dose related to diclofenac sodium was 0.5 mg/kg.

Heparinized blood samples were taken from the animals by heart punction and diclofenac concentration was determined from the plasma separated by centrifugation following appropriate purification (solid phase extraction) and analysis by HPLC.

Results are shown in Table V. The plasma concentration of diclofenac in rabbits treated with the complex was higher at every time point (between 0.5–4 hours) than that of diclofenac-treated animals.

TABLE V

Absorption of diclofenac in rabbits following oral
administration of diclofenac sodium and diclofenac sodium/g-
cyclodextrin complex of 1:2 molar ratio
dose related to diclofenac sodium: 0.5 mg/kg

| | Diclofenac (ng/ml) | | | | | | | |
|---|---|---|---|---|---|---|---|---|
| | Diclofenac sodium | | | | Complex | | | |
| Time | Serial No. of animals | | | | | | | |
| (h) | 7 | 8 | 9 | X | 10 | 11 | 12 | X |
| 0 | 0 | 0 | 0 | 0 | 0 | 0 | 0 | 0 |
| 0.5 | 248.15 | 192.35 | 340.25 | 260.25 | 251.98 | 259.31 | 338.75 | 283.35 |
| 1 | — | 121.53 | 158.02 | 139.77 | 157.78 | 198.97 | 275.32 | 210.69 |
| 2 | 120.19 | 80.425 | 91.75 | 97.45 | 110.38 | 93.99 | 174.44 | 126.27 |
| 3 | 48.25 | 50.42 | 49.71 | 49.46 | 70.27 | 97.39 | 98.75 | 88.80 |
| 4 | 16.44 | 82.45 | 49.54 | 49.48 | 60.54 | — | 82.16 | 71.35 |

The results of the absorption study indicate that both absorption and bioavailability as well of diclofenac can be improved by γ-cyclodextrin complexation of the drug.

EXAMPLE 5

From the diclofenac sodium/γ-cyclodextrin complex ("B" composition) tablets were prepared by the usual method, direct compression and using the usual excipients as follows:

| | | |
|---|---|---|
| diclofenac sodium/γ-cyclodextrin complex (25 mg diclofenac sodium) | 31.6 kg | (73.49%) |
| microcrystalline cellulose | 9.0 kg | (20.93%) |
| crosslinked polyvinyl pyrrolidone | 2.0 kg | (4.65%) |
| magnesium stearate | 0.4 kg | (0.93%) |
| | 43.0 kg | (100%) |

The complex and the excipients were homogenized and pressed to tablets directly. The amount given above is enough for production of 100,000 tablets.

What is claimed is:

1. A composition comprising 50% or more by weight of a first inclusion compound formed from diclofenac or a pharmaceutically acceptable salt thereof and gamma-cyclodextrin at a molar ratio of about 1:2.

2. A composition according to claim 1, wherein a remaining portion of said composition which is not said inclusion compound comprises one or more ingredients selected from the group consisting of diclofenac, a further inclusion compound formed from diclofenac and a cyclodextrin other than an inclusion compound formed from diclofenac and gamma-cyclodextrin at a molar ratio of about 1:2, or mixtures thereof.

3. A composition according to claim 2, wherein said remaining portion comprises a second inclusion compound formed from diclofenac and gamma-cyclodextrin at a molar ratio of about 1:1.

4. A composition according to claim 2, wherein the composition comprises at least 80% by weight of said first inclusion compound.

5. A composition according to claim 2, wherein the composition comprises at least 90% by weight of said first inclusion compound.

6. A composition according to claim 2, wherein the composition comprises at least 95% by weight of said first inclusion compound.

7. A composition according to claim 1, wherein the composition comprises at least 80% by weight of said first inclusion compound.

8. A composition according to claim 1, wherein diclofenac is present as its sodium salt.

9. A pharmaceutical preparation comprising the inclusion compound of claim 1 together with one or more customary pharmaceutical adjuvants.

10. A pharmaceutical preparation according to claim 9, wherein the preparation is a dry preparation in the solid state.

11. A pharmaceutical preparation according to claim 9, wherein the preparation is acceptable for oral ingestion.

12. A pharmaceutical preparation according to claim 9, wherein the preparation is a granulate, a non-effervescent tablet, or an effervescent tablet.

13. A composition according to claim 1, wherein the composition comprises at least 90% by weight of said first inclusion compound.

14. A composition according to claim 1, wherein the composition comprises at least 95% by weight of said first inclusion compound.

* * * * *